United States Patent [19]

Charles et al.

[11] 4,088,946
[45] May 9, 1978

[54] MAGNETIC BRIDGE TRANSDUCER FORMED WITH PERMANENT MAGNETS AND A HALL EFFECT SENSOR FOR IDENTIFYING THE PRESENCE AND LOCATION OF FERROMAGNETIC DISCONTINUITIES WITHIN OR ON A TUBULAR SPECIMEN

[75] Inventors: Robert G. Charles, Allison Park; William T. Lindsay, Jr., Irwin, both of Pa.

[73] Assignee: Westinghouse Electric Corp., Pittsburgh, Pa.

[21] Appl. No.: 599,499

[22] Filed: Jul. 28, 1975

[51] Int. Cl.² .................................. G01R 33/12
[52] U.S. Cl. ................................ 324/220; 324/232; 324/235
[58] Field of Search ............... 324/37, 41, 45, 34 TK, 324/34 D, 34 PS; 338/32 R, 32 H

[56] References Cited

U.S. PATENT DOCUMENTS

| 2,897,438 | 7/1959 | Fearon | 324/34 R |
| 3,060,370 | 10/1962 | Varterasian | 324/45 |
| 3,340,467 | 9/1967 | Ha | 324/41 |
| 3,676,828 | 7/1972 | Masuda et al. | 338/32 H |

FOREIGN PATENT DOCUMENTS 974,516  11/1964  United Kingdom ............... 324/45

Primary Examiner—Robert J. Corcoran
Attorney, Agent, or Firm—D. C. Abeles; Z. L. Dermer

[57] ABSTRACT

A transducer for identifying and quantitatively measuring the presence and location of ferromagnetic material, which is specifically suitable for remotely mapping ferromagnetic deposits on pressurized water reactor steam generator tubing. The transducer employs a first source of a magnetic field which is positionable in magnetic communication with and is mounted to be movable over the surface area of the workpiece. Perturbations produced in the magnetic field as a result of ferromagnetic discontinuities associated with the workpiece are sensed by a Hall element fixedly positioned with respect to the source in magnetic communication with the workpiece. Means are provided for altering the magnetic field of the source in communication with the Hall element to substantially null the output of the Hall element in the absence of magnetic material within or on the workpiece within proximity of the Hall element.

12 Claims, 4 Drawing Figures

U.S.Patent  May 9, 1978  Sheet 2 of 2  4,088,946

4,088,946

MAGNETIC BRIDGE TRANSDUCER FORMED WITH PERMANENT MAGNETS AND A HALL EFFECT SENSOR FOR IDENTIFYING THE PRESENCE AND LOCATION OF FERROMAGNETIC DISCONTINUITIES WITHIN OR ON A TUBULAR SPECIMEN

BACKGROUND OF THE INVENTION

This invention pertains generally to magnetic probes and more particularly to such transducers incorporating magnetic bridge arrangements which are operable to map ferromagnetic discontinuities within or on a specimen.

There presently exists a need for determining the buildup of corrosion products ("sludge") on the outer surfaces of steam generator tubing which will, if undetected, reduce the efficiency of the operating components. This is particularly important in pressurized water reactor electrical generating facilities where the problem is complicated by lack of direct access to the outer surfaces of the steam generator tubes when the tubes are in place. In addition, in such an application, remote monitoring is a necessity to avoid exposure to radiation. Any measuring device which is to be employed in such an application therefore must function when inserted inside the coolant tubes. In other words, such a device must be capable of sensing corrosion products when separated from these materials by the metal walls of the heat exchanger tubing. The requirement that such a probe function when separated from the material to be monitored by a continuous metallic wall is a particularly stringent one, since it rules out most of the experimental approaches which might otherwise be employed.

The corrosion products which are formed under reactor conditions are known to contain, as the major component, $Fe_3O_4$, a strongly ferromagnetic substance. Ferromagnetism therefore suggests itself as a physical property which can be measured to provide a map of the sludge buildup on the outer surfaces of steam generator tubing in pressurized water reactor electrical generating facilities.

Apparatus for the remote detection of magnetic materials can be classified into two groups, depending on whether they are implemented through the use of static or of periodically varying magnetic fields. While the latter group of methods can be made quite sensitive, their use is complicated by an inherent sensitivity to materials of high electrical conductivity such as are employed in steam generator tubing walls, whether these materials are also magnetic or not. The conductive metallic wall between the probe and the deposits therefore forms a source of interference. Since the use of static magnetic fields does not present this problem such probes are desirable in this particular application.

In addition, a probe is desired that is capable of detecting small discontinuities associated with thin films of sludge deposits. Further, in order to supply complete information on the buildup of deposits on the outer surface of steam generator tubing it is desired that such probes be directionally sensitive to the radial distribution of the deposits as well as the longitudinal deposit distribution along the length of the steam generator tubing.

SUMMARY OF THE INVENTION

Briefly, this invention satisfies the above criteria by providing a transducer that is capable of identifying the presence and location of ferromagnetic discontinuities within or on a workpiece. The transducer of this invention is remotely operable to quantitatively measure the ferromagnetic properties of materials within or on the workpiece; and, in one embodiment in an application to elongated tubular workpieces, the transducer of this invention provides information on not only the longitudinal distribution along the axial length of the workpiece, but the radial ferromagnetic distribution around the circumference as well.

More specifically, the transducer of this invention generates a magnetic field which can be placed in magnetic communication with and is movable over a portion of the surface area of the workpiece. A Hall element within the transducer is fixedly positioned with respect to the source of the magnetic field and arranged to be placed in magnetic communication with the specimen. The output of the Hall element which provides the transducer response is representative of the strength of the magnetic field having a component contribution from lines of force proximate and perpendicular to a given plane of the Hall element. Means are provided for altering the magnetic field of the source within the transducer in magnetic communication with the Hall element to substantially null the output of the Hall element in the absence of the ferromagnetic material within or on the workpiece being surveyed. Discontinuities in the ferromagnetic characteristics of the workpiece along its surface will alter the magnetic field affecting the Hall element and effect an electrical output quantitatively representative of the ferromagnetic discontinuity.

In the specific application to elongated tubular workpieces the transducer is sized to fit within the workpiece and designed to provide a uniform magnetic field around its circumference, which when altered by a ferromagnetic discontinuity along the longitudinal length of the specimen, will affect the Hall element output. In a second embodiment the Hall element and source are designed to be sensitive to the radial distribution of the ferromagnetic characteristics of the workpiece. In this way a complete map can be made of the ferromagnetic characteristics of the workpiece and its surface deposits.

BRIEF DESCRIPTION OF THE DRAWINGS

For a better understanding of the invention, reference may be had to the preferred embodiment, exemplary of the invention, shown in the accompanying drawings, in which.

DESCRIPTION OF THE PREFERRED EMBODIMENT

Figure 1:
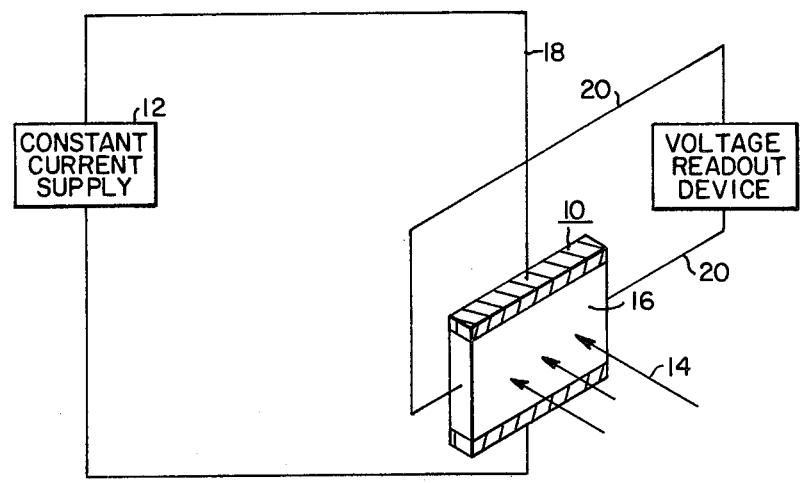
FIG. 1 is a schematic illustration of Hall-effect element employed in the transducer of this invention for measuring magnetic field strength.

The apparatus of this invention uniquely satisfies the need for a sensing probe which can remotely monitor the ferromagnetic distribution of materials within or on a workpiece. Unique benefit is achieved specifically in an application to detecting and mapping the distribution of sludge on the inaccessible outer tube surfaces of pressurized water reactor steam generators. The requirement that the probe function remotely, when separated from the material to be monitored by a continuous metallic wall is a particularly stringent one. The apparatus of this invention circumvents these obstacles by making use of the ferromagnetic properties of the sludge deposits.

Methods for remote detection of magnetic materials can be generally classified into two groups as previously explained. Probes employing static magnetic fields are specifically suitable for such remote isolated applications. Further simplification is achieved by employing small permanent magnets to generate the static fields required. Desirably, the intervening tube material of the workpiece should be substantially non-magnetic; though, some residual magnetism can be tolerated. Fortunately, Inconel 600, the material generally employed in the construction of steam generator tubes for pressurized water reactors, is substantially non-magnetic.

The apparatus of this invention functions by sensing the perturbations produced in the magnetic field generated by a small permanent magnet when the magnet is brought into close proximity to ferromagnetic sludge. The perturbations are sensed and converted to an electrical output by means of a commercially available Hall-effect element. In principle, the simple arrangement of a Hall element disposed between the poles of a magnet could be employed as a probe. In practice, however, this configuration is not satisfactory because of the large electrical output signal which is obtained even in the absence of magnetic sludge. An important aspect of this invention is the means adopted to obviate this undesirable characteristic to increase greatly the effective sensitivity of such probes.

Basically, the apparatus of this invention balances magnetic fields, within the probe itself, in such a way that a zero magnetic field is sensed at the Hall element when the probe is remote from external ferromagnetic materials. Internal balancing of this kind confers inherent insensitivity to external disturbances such as temperature changes. When a probe, initially balanced in this manner, is brought near a ferromagnetic material, the resulting electrical signal is a direct measure of the perturbation produced in the magnetic field and hence is also a measure of a quantity of ferromagnetic material present. This type of arrangement can be analogized generally to the electrical bridge arrangements, as exemplified by the familiar Wheatstone bridge circuit which is often used to measure electrical resistance changes.

The heart of the embodiments to be described, and the component which actually generates an electrical output, is a commercially available Hall effect element. Such elements are available, relatively inexpensively, from a number of commercial suppliers, i.e., F. W. Bells' Model BH-700, Columbus, Ohio.

Hall-effect elements, such as the one illustrated by reference character 10 in FIG. 1, make use of the well known fact that an electrical potential (Hall potential) is induced across an electrical conductor when a direct current flows through it and it is simultaneously subjected to a magnetic field. The magnitude of the Hall potential is a function of the current 12, the strength of the magnetic field 14 and the material making up the conductor 16. These quantities are related by the following relationship:

$$V_H = kIH$$

where $V_H$ is the Hall potential, $I$ is the current, $H$ is the component of magnetic field strength perpendicular to the surface of the conductor, and $k$ is a constant characteristic of the material which makes up the conductor. The constant $k$ is very small for metals but is much larger for certain semiconductors, with indium arsenide being the material of choice for most commercial elements, including the exemplary element illustrated.

The typical Hall element illustrated in FIG. 1 includes a small plastic encapsulated, thin rectangular plate of indium arsenide 16 with four attached electrical leads. Two of the electrical leads 18 introduce a constant current across the indium arsenide conducting plate and the remaining two leads 20 are employed to measure the resulting Hall potential. For the Bell Model BH-700 element, a suitable current is 200 milliamps and the measured Hall voltage is approximately 50 microvolts per gauss for fields ranging from a fraction of a gauss to the kilogauss range. From the above equation it is apparent that sensitivity can be increased by using as large a current as possible. The practical upper current limit is dictated by the self-heating characteristics of the element as well as by the heat sinking characteristics of its environment. The exemplary element set forth can be operated continuously in air at a current of 200 milliamps. For maximum accuracy it is important that the current be held constant. This is best accomplished by means of a powder supply specifically designed for constant current operation. However, a constant voltage supply is satisfactory if a suitable resistor is placed in series with the element to limit the current.

This invention takes advantage of several of the less obvious characteristics of Hall elements to provide the desired sensitivity required in a stringent application to remote monitoring of sludge deposits. The first important characteristic of Hall elements is that they respond only to the component of a magnetic field which is perpendicular to the surface of the element. It follows that an element placed in a magnetic field with the plane of the semiconductor slab parallel to the lines of force will give a zero voltage output, even when very high fields of strength are involved. A second characteristic of such elements is that they can give either a positive or a negative Hall voltage output, depending both on the direction of current flow and the direction of the magnetic field. Reversing either the current or the field gives an output which is unchanged in magnitude but opposite in sign. If both current and magnetic field are fixed, rotating the Hall element 180° will produce the same effect. A third desirable characteristic of such elements are that they are inherently low noise devices, at least partially due to their low electrical resistivities. This characteristic makes practical their use even when the voltage output is in the low microvoltage range, provided one employs suitable low noise electronic amplification.

The basic principle underlying the embodiments of this invention to be described, is the use of the Hall element to measure the perturbation produced in the magnetic field of a permanent magnet when the magnet is brought into close proximity to ferromagnetic corrosion products. In theory, the simple arrangement previously described might be used to measure such perturbation. However, the Hall element in such an arrangement gives a voltage output proportional to the magnetic flux density between the two permanent magnetic poles. If, now, a ferromagnetic object is brought near one of the poles, the magnetic flux density between the poles will be altered. The difference in the two voltage readings should then be a measure of the amount of ferromagnetic material present.

In practice, the above device will be far too insensitive for an application to measure sludge deposits. A large Hall potential will be measured even in the absence of ferromagnetic material; and the measured voltage will undergo only a small fractional change for the amounts of ferromagnetic material of interest in the sludge. Thus, in such a simple arrangement as that set forth above, one encounters the usual problems associated with measuring a small change in a large quantity. The obvious solution to circumvent this difficulty is to buck out the portion of the measured potential not associated with the presence of ferromagnetic material by means of an external voltage source connected in series opposition to the Hall element. This is not a practical solution, however, because of the sensitivity of such an arrangement to environmental disturbances. A change in the ambient temperature, for example, is likely to affect the Hall element quite differently from its effect on the external voltage source, even assuming both components equilibrate with the new temperature at equal rates. The net results are drifting of the measured difference voltage and unacceptably large noise levels.

This invention employs a more effective approach to increasing the sensitivity of the Hall output by subjecting the Hall element to a balance magnetic bridge circuit which renders a zero voltage output in the absence of the magnetic material to be measured. A number of different magnetic bridge arrangements could be employed to effect this approach by utilizing some of the unique properties of Hall elements set forth above. In a sense, this approach also makes use of "bucking out" techniques. The important difference is that with the design of this invention, the resulting device becomes relatively insensitive to extraneous perturbations, such as temperature changes, since opposing parts of the "magnetic circuit" are effected to an opposite and nearly equal degree by such disturbances.

Figure 2:
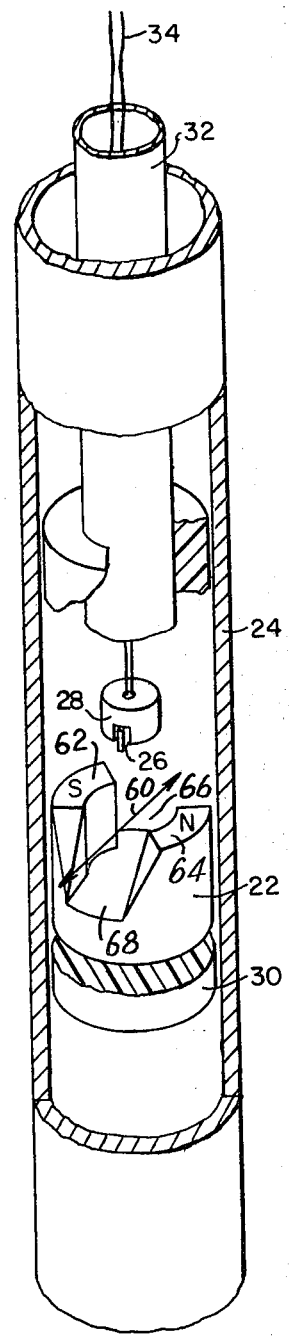
FIG. 2 is a perspective view of one embodiment of the transducer of the invention.

FIG. 2 illustrates one embodiment of this invention which provides the desired characteristics outlined above. The specific arrangement illustrated is designed for application to tubular workpieces, though it can be appreciated that the probe thus shown can be modified to monitor workpieces of other geometries. Basically, the probe of this embodiment is similar to the basic configuration previously identified employing a first cylindrical magnet 22 which is sized to mate with the inside diameter of the wall 24 of the tubular workpiece with enough tolerance to establish a sliding fit. A Hall-effect element 26 is disposed between and spaced from the poles of the magnet 22 and aligned so that the magnetic lines of force communicating between the poles perpendicularly bisect the plane of the Hall element. The modification to the basic configuration previously described is established by the addition of a second, smaller, cylindrical, permanent magnet 28 which is disposed in proximity to the Hall element and aligned so that its magnetic lines of force communicated through the Hall element are equal and opposite to that established through the Hall element by the larger magnet 22; thus establishing a zero magnetic field across the Hall element and an initial electric null Hall output. The proper clearance between the probe and the inside of the tubing to be monitored is important. Too close a fit can result in output errors due to radial motion of the probe, with respect to the walls of the surrounding tube. When the fit is too tight the probe acts as a strain gauge giving large spurious outputs which reflect the stress on the probe components. With proper clearance the probe should slide easily within the surrounding tubing without obvious wobble or binding. Exemplary magnets which can be used in such a configuration are Models 5H-148 and S2H-613 of the Arnold Engineering Company, Marengo, Illinois. By mounting the smaller magnet 28 much closer to the Hall element than the larger magnet, a position can be found where the effects of the two magnetic fields exactly cancel and the measured Hall potential is close to zero. In practice, this is best done by trial and error positioning during assembly or by cementing small pieces of magnetic foil near the magnet poles after assembly, as required to give balance. The diameter of the smaller of the two magnets 28 is desirably chosen so that its contribution to the magnetic field perpendicularly bisecting the Hall element 26 is substantially unaffected by materials within or on the walls of the workpiece.

The complete assembly is encapsulated in an epoxy resin 30 which maintains the spacing and alignment of the magnets and Hall element. The resin is formed to provide the same spacing required for the larger of the two magnets 22. The electrical leads 34 from the Hall element are brought out through the smaller of the two magnets 28 through a non-magnetic support tube 32 to the driving and readout electronics.

When a ferromagnetic object is placed in proximity to either pole of the lower magnet of the embodiment shown in FIG. 2, the initial magnetic field symmetry is upset and a net Hall voltage results. It is an important characteristic of this invention that the voltage response for a given object is the same at either magnetic pole, both in magnitude and in sign. The device, therefore, has nearly equal sensitivity for ferromagnetic material at any point around the perimeter of the circle defined by the outer edges of the two lower magnetic poles. The sensitive region of the device is approximately as shown between the two extremes of the magnets 22 and 28.

A complicating property, however, of the apparatus of FIG. 2 is that a Hall voltage output also results when a ferromagnetic object is near the poles of the smaller, upper magnet 28. The output characteristic of the upper magnet is moreover of opposite sign to those given at the lower magnet. The design of the device, is, thus, basically a differential one. Indeed, a fully differential response, based on the difference in amount of ferromagnetic material near the upper magnet as opposed to the lower, would result were the two magnets of the embodiment illustrated in FIG. 2 of equal size. For an application to mapping sludge deposits on steam generator tubing, an absolute, rather than a differential response is required. This result is achieved by employing a small jdiameter magnet as the upper source 28, sized so that its magnetic field communicated through the Hall element is substantially unaffected by the workpiece being monitored. By sufficiently increasing the physical separation between the upper magnet poles and the surrounding magnetic corrosion products, the upper magnet becomes relatively insensitive to the external environment while still retaining its essential function of producing an initial null.

Thus, by longitudinally moving the probe illustrated in FIG. 2 along the axis of revolution of the tubular workpiece, an axial map of the ferromagnetic distribution along the tubing walls can be obtained. It can be readily recognized that remote drives such as are used for in-core flux monitors can be employed to move the probes to provide a completely remotely operated device.

Figure 3:
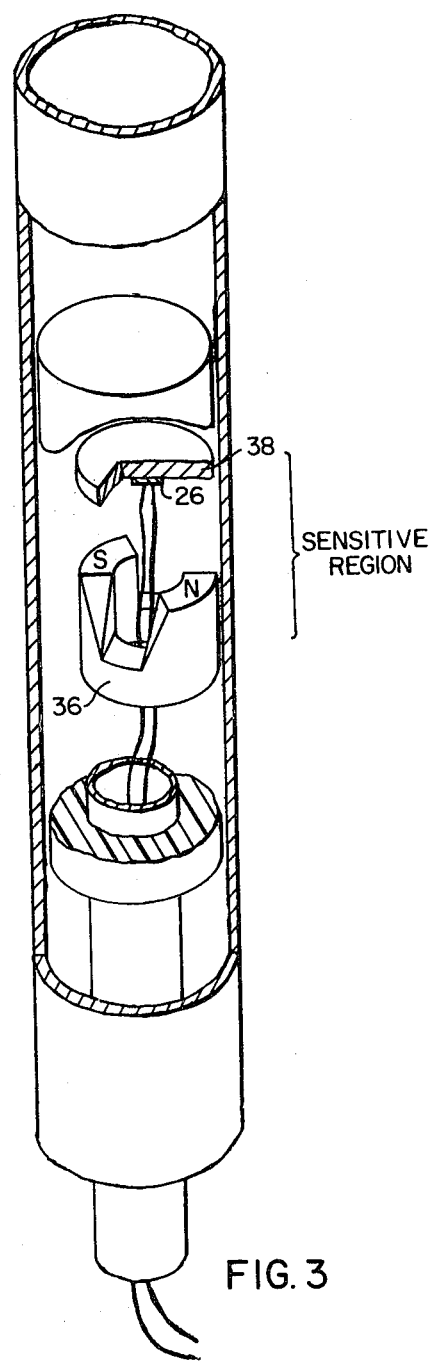
FIG. 3 is a perspective view of a second embodiment of this invention.

FIG. 3 illustrates a second embodiment of this invention which provides not only a longitudinal map of the ferromagnetic discontinuities along the workpiece, but a map of the radial distribution as well. The probe, like that of the embodiment illustrated in FIG. 2, utilizes a single Hall element 26, but differs in that it is designed to have radial directional sensing properties. The magnetic field in this embodiment is generated by a single source 36, for example, a small horseshoe shaped Alnico magnet (Sears Roebuck Catalog No. 9KT40361) which is deliberately mounted offcenter of the annular opening of the tubular workpiece to be monitored. Mounted above the magnet, and coaxial with it, is a soft iron disc, for example, the "keeper" accompanying the magnet. The Hall element 26 is cemented flat against the undersurface of the disc, at its center as shown in FIG. 3 which is perpendicular to the Hall element's position illustrated in FIG. 2. With this arrangement, assuming perfect symmetry, voltage output of the Hall element is zero, since the large Hall potential which would be induced, were the north magnetic pole present alone, is exactly counterbalanced by the presence of the south pole at an equal distance. In practice, the actual voltage output of the element is very sensitive to errors in positioning of the element during assembly or to assymetries inherent in the magnet or iron disc. The best way to attain an initial satisfactory null is to make small adjustments in positioning while the epoxy cement, which is employed to hold the magnet-Hall element-iron disc assembly, is setting. During this time the Hall voltage output can be continuously monitored. A second method is to cement the three parts of the assembly together, using measurement alone. Final adjustment of the null can be obtained by trial and error, using small pieces of iron or Mu-metal foil cemented, offcenter, to the undersurface of the disc. Mu-metal is one of several trade names for commercially available iron-nickel alloys having high magnetic permeabilities. By one or the other, or a combination of these methods, it is relatively easy to reduce the null Hall voltage to 100 microvolts or less. A still better null can be obtained, during actual measurements, by applying an appropriate small bucking potential from an external source. The bucking potential required is only a small fraction of that which would be necessary for the simple basic arrangement previously described. Hence, the objections pointed out previously to bucking out techniques do not apply. This small bucking potential can be used for final zeroing when the probe is in place within the heat exchanger tubing being monitored to counter any residual magnetism which may be established in the materials of the tubing. The epoxy encapsulation which supports the probe assembly is gauged to provide the same sliding fit specified for the embodiment illustrated in FIG. 2. Similarly, a non-magnetic support cable containing the electrical leads is brought out to form the drive for the probe.

The magnetic Hall element-disc assembly illustrated in FIG. 3 is, like the configuration of FIG. 2, basically a differential arrangement. A ferromagnetic object brought near either magnetic pole produces a net Hall voltage, but the sign of the measured response is, in this incidence, opposite for the two poles. The soft-iron disc 38 is employed to concentrate lines of force through the Hall element parallel to the plane of the element. The reason for mounting the assembly offcenter, relative to the surrounding tube, is to make it physically impossible for the magnetic corrosion products monitored to approach the south magnetic pole. The response of the device falls off sufficiently fast with distance from a magnetic object that the south pole becomes essentially insensitive to corrosion products on the tubing with the relative dimensions illustrated. The result is that the sensor is effectively a directional one, responding only to magnetic materials on that part of the tubing which is immediately adjacent to the north magnetic pole. It should be appreciated that the sensor would operate equally as well if the poles of the magnet 36 were rotated 180°. Thus, a map of the radial distribution is obtained by rotating the probe 360° around the inner circumference of the tubular workpiece. After each radial distribution measurement is obtained, the probe is advanced longitudinally a distance approximately equal to the sensitive region of the sensor and the radial distribution measurement is repeated. Employing a drive system, such as are employed in the in-core flux monitoring systems of nuclear reactors, a full distribution map can be obtained with reference coordinates over the entire surface area of the workpiece under inspection.

Current is best supplied to the Hall element by means of a constant current supply, such as the Model 920 constant current supply in combination with a Model 292 power booster manufactured by California Electronic Corporation, Alamo, California. If a constant current supply is not available, a constant voltage supply, in series with a variable resistor, can be substituted. For example, the small modular and inexpensive regulated five volt dc supplies which are sold for use with digital logic circuits are very suitable for the above application when employed in series with a twenty-five ohm rheostat. The output Hall voltage of the two embodiments illustrated in FIGS. 2 and 3 can be measured by any suitable instrument capable of measuring these signals in the millivolt and microvolt range which has a reasonably high input impedance. For the ultimate in sensitivity and stability, however, high quality instrumentation is required, since the low noise level characteristic of Hall elements often makes the readout instrumentation the limiting factor in determining the maximum practical sensitivities of the transducer arrangements. Other factors which influence the lowest levels of magnetic material which can be detected by the embodiments of this invention include: the sensitivity and constancy of extraneous magnetic fields, including that due to the earth itself; the presence and uniformity of distribution of residual magnetism in the metal walls of the heat exchanger tubing; and how good a tradeoff between "wobble" and "binding" can be effected in fitting the sensor to the inside of the tube to be monitored.

Experimental results have been obtained employing a Keithley Model 150B microvolt meter manufactured by Keithley Instruments, Inc., Cleveland, Ohio. By this means meaningful Hall element outputs have been obtained well below the ten microvolt level. Such instruments are also convenient in that they include a built-in voltage source for bucking out the small zero-point outputs of the devices which become significant when the highest sensitivities are required.

Figure 4:
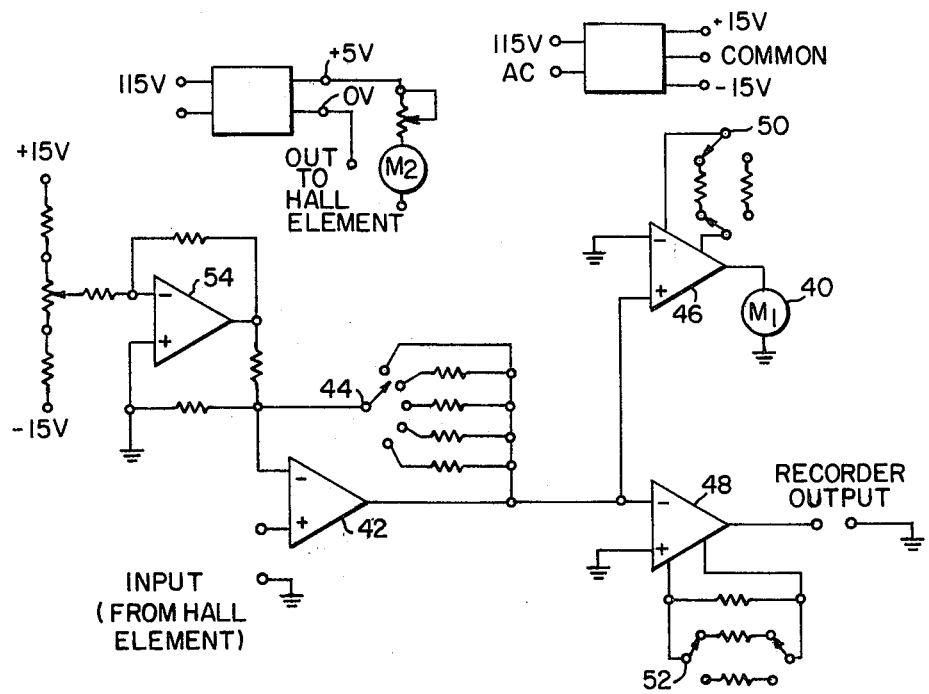
FIG. 4 is a circuitry schematic of the readout electronics of the transducer of this invention.

A circuit for a much more portable and less expensive combination readout-meter-power supply, for use with the embodiments of this invention is shown in FIG. 4. The circuit illustrated gives results equivalent to those obtained with the more sophisticated Keithley instrument for voltage readings down to approximately 20 microvolts.

The circuit schematically illustrated in FIG. 5 employs a miniature chopper operational amplifier 42, such as the Burr Brown 3480 chopper operational amplifier manufactured by the Burr Brown Research Corp., Tucson, Arizona, for the initial preamplification of the Hall potential output. The degree of amplification can be varied, as shown by the switch 44. Additional amplification for the readout meter 40 is provided by the modular instrumentation amplifier 46 which can be any one of a number of commercially available amplifiers such as the Burr Brown 3061-25 instrumentation amplifier. Instrumentation amplifier 48 provides a separate and non-interacting recorder output. Accordingly, the meter and the recorder can be used separately or simultaneously. The degree of amplification for the meter or recorder can be varied independently by corresponding switches 50 and 52. Integrated circuit operational amplifier 54 which is a commercially available item such as the Fairchild $\mu$ 74IC operational amplifier, manufactured by the Fairchild Semiconductor, Mountainview, California, provides a stable voltage also at either the recorder or meter terminals. Desirably, the range of offset is sufficient to allow use of the meter in either a zero-center or a zero-left mode. The power supplies P1 and P2 are respectively employed to drive the Hall effect element and amplifiers for the readout electronics. It should be understood that the circuit values illustrated are exemplary and will vary with the components employed.

The Hall voltage output from the transducers of this invention is a function both of the quantity and type of ferromagnetic material adjacent the sensitive region of the probe. To obtain quantitative information on the extent of corrosion product buildup it is necessary, therefore, to calibrate the device in terms of the ferromagnetic species expected. In a particular application to mapping sludge deposits on the exterior walls of steam generator tubing there is generally only one species of ferromagnetic material of interest, $Fe_3O_4$. Thus, after calibration, reliable quantitative measurements can be obtained.

A slight decrease in response of the transducer shown in FIG. 2 when ferromagnetic material is opposite the two gaps 66 and 68 between the magnetic poles 62 and 64 can be compensated for by grinding the circumferential surface of the magnet 22 to a slightly elliptical cross section, with the major axis 60 bisecting the gaps 66 and 68 between the magnetic poles 62 and 64. This type of configuration will slightly decrease the response when ferromagnetic material is adjacent to the magnetic poles 62 and 64 as compared to the response when the magnetic material is adjacent the gaps 66 and 68 of the magnets. Thus, uniformity of response is achieved with this additional improvement by compensating for the more sensitive region adjacent the magnetic poles.

Thus, the embodiments of this invention provide apparatus for remotely, quantitatively mapping ferromagnetic discontinuities within or on a workpiece with a high degree of sensitivity.

What is claimed is:

1. Apparatus for identifying the presence and location of ferromagnetic discontinuities within or on a tubular specimen comprising:

a first source of a static magnetic field sized to slidably fit within the tubular specimen and constructed to generate a radially directed magnetic field having a substantially uniform strength 360° around a given axis parallel to the axis of revolution of the specimen and positioned to permit movement along the given axis with the magnetic flux generated in communication with the specimen wall;

a Hall element in magnetic communication with and fixedly positioned with respect to the first source and arranged to be in magnetic communication with the specimen as part of a magnetic loop where the magnetic flux communication path through the specimen extends in series between the first source, the specimen and the Hall element, the Hall element having an output representative of the strength of a magnetic field having a component contribution from lines of force proximate and perpendicular to a given plane of the Hall element; and means for altering the magnetic field of the first source in magnetic communication with the Hall element to substantially null the output of the Hall element in the absence of ferromagnetic discontinuities within or on the specimen along the series flux path, said means for altering the magnetic field being fixedly positioned with respect to the Hall element.

2. The apparatus of claim 1 wherein the first source is positioned to communicate magnetic lines of force through the Hall element perpendicular to the given plane.

3. The apparatus of claim 2 wherein the means for altering the magnetic field comprises a second source of a magnetic field positioned to communicate magnetic lines of force through the Hall element of equal strength and of opposite polarity to the lines of force communicated through the Hall element by the first source.

4. The apparatus of claim 3 wherein the first and second sources comprise corresponding first and second magnets.

5. The apparatus of claim 4 wherein the first magnet is positioned proximate the specimen and spaced from the Hall element, and the second magnet is positioned proximate the Hall element and spaced from the specimen, the respective first and second magnets are sized and arranged to communicate substantially equal and opposite magnetic lines of force through the given plane of the Hall element and the proximity to the Hall element and spacing from the specimen of the second source is gauged to substantially direct the magnetic field of the second magnet communicated to the Hall element substantially through a flux communication path that does not include ferromagnetic material within or on the specimen.

6. The apparatus of claim 4 wherein the first and second sources comprise corresponding first and second permanent magnets.

7. The apparatus of claim 1 wherein the means for altering the magnetic field of the first source comprises means for substantially directing the magnetic lines of force communicated to the Hall element from the first source parallel to the given plane of the Hall element.

8. The apparatus of claim 7 wherein the means for directing the magnetic field of the first source comprises a soft iron core positioned proximate to the Hall element and designed to concentrate the magnetic lines of force parallel to the given plane.

9. The apparatus of claim 1 for quantitatively measuring ferromagnetic deposits on the surface of the specimen wherein the means for altering the magnetic field nulls the output of the Hall element when the apparatus is in measuring proximity of the specimen absent such deposits.

10. The apparatus of claim 1 wherein the first source comprises a permanent magnet having an elliptical circumference with the center of the ellipse designed to be positioned coextensive with the axis of revolution of the specimen and the minor axis of the ellipse extending perpendicular to the axis of revolution of the specimen between the poles of the magnet.

11. The apparatus of claim 1 wherein the first source and the Hall element are constructed to be situated a fixed distance from the axis of revolution of the specimen, sized to render the Hall element radially sensitive when situated within the specimen and mounted to permit rotation around the axis of revolution.

12. The apparatus of claim 11 wherein the first source and the Hall element are mounted to move along an axis parallel to the axis of revolution of the specimen spaced at the fixed distance therefrom.

* * * * *